United States Patent [19]

McGhee et al.

[11] Patent Number: 5,157,930

[45] Date of Patent: Oct. 27, 1992

[54] ORGAN PRESERVATION APPARATUS

[76] Inventors: Samuel C. McGhee; C. Lester McGhee, both of P.O. Box 1953, Sugar Land, Tex. 77478

[21] Appl. No.: 688,973

[22] Filed: Apr. 22, 1991

[51] Int. Cl.[5] .......................... B01F 3/04; F24F 3/16; F04B 43/00
[52] U.S. Cl. .......................................... 62/78; 62/64; 62/306
[58] Field of Search .................. 62/64, 78, 306; 417/472-475; 431/1

[56] References Cited

U.S. PATENT DOCUMENTS

| | | | |
|---|---|---|---|
| 3,545,221 | 12/1970 | Swenson et al. | 62/78 X |
| 3,545,225 | 12/1970 | Swenson et al. | 62/78 X |
| 3,607,646 | 9/1971 | de Roissart | 62/306 X |
| 3,632,473 | 1/1972 | Belzer et al. | 195/1.7 |
| 3,753,865 | 8/1973 | Belzer et al. | 195/127 |
| 3,777,507 | 12/1973 | Burton et al. | 62/306 |
| 3,896,501 | 7/1975 | Bifano et al. | 417/472 X |
| 3,914,954 | 10/1975 | Doerig | 62/306 |
| 3,995,444 | 12/1976 | Clark et al. | 62/306 |
| 4,186,565 | 2/1980 | Toledo-Pereyra | 62/306 |
| 4,239,464 | 12/1980 | Hein | 417/474 |
| 4,242,883 | 1/1981 | Toledo-Pereyra | 62/78 X |
| 4,249,923 | 2/1981 | Walda | 62/78 X |
| 4,462,215 | 7/1984 | Kuraoka et al. | 62/78 |
| 4,471,629 | 9/1984 | Toledo-Pereyra | 62/78 X |
| 4,494,385 | 1/1985 | Kuraoka et al. | 62/306 |
| 4,549,860 | 10/1985 | Yakich | 417/475 |
| 4,745,759 | 5/1988 | Bauer et al. | 62/64 X |
| 4,925,377 | 5/1990 | Inacio et al. | 417/472 |
| 5,044,901 | 9/1991 | Fumero et al. | 417/474 |

OTHER PUBLICATIONS

"MOX-100 Renal Preservation System" Waters Instruments, Inc. 1982.
"Ultrasonic Air Bubble Detectors", Zevex, Inc.
"Flexible Ceramic Coatings and Coating Systems" Insulated Coatings Corp.

Primary Examiner—Henry A. Bennet
Assistant Examiner—Christopher Kilner
Attorney, Agent, or Firm—Harrison & Egbert

[57] ABSTRACT

An organ preservation apparatus including an organ-receiving chamber, a pulsatile pump in continuous uninterrupted liquid communication with the organ-receiving chamber, and a fluid delivery tube interconnected between the organ-receiving chamber and the pulsatile pump for passing the organ preservation fluid from the organ-receiving chamber to the pulsatile pump. The pulsatile pump is configured to pass an organ preservation fluid to the organ-receiving chamber in a dichrotic pulse pattern. The organ-receiving chamber has an outer box with an insulated interior area, an organ-receiving cassette removably contained within the insulated interior area, and a lid detachably fastened to the outer box. The pulsatile pump includes a bladder pump, a motor, and a cam connected to the motor. The cam is connected to an actuator so as to compress the bladder pump is a dichrotic pulse pattern. A pressure transducer is connected to the fluid passageway between the pulsatile pump and the organ-receiving chamber so as to measure diastolic and systolic fluid pressure.

26 Claims, 4 Drawing Sheets

ORGAN PRESERVATION APPARATUS

TECHNICAL FIELD

The present invention relates to methods and apparatus for preserving human organs outside of the body. More particularly, the present invention relates to apparatus suitable for the transport and storage of human organs prior to transplantation.

BACKGROUND ART

Heretofore, there have been many difficulties and inconveniences in the process of transplanting human organs from one person to another. For example, patients waiting to receive an unrelated donor kidney have to be on constant standby in the hospital, sometimes for weeks. When the donor appeared, the timing was very important, for the surgery had to be substantially simultaneous so that immediately upon removal of the kidney from the donor, it could be transplanted into the patient. This meant that there had to be at least two surgical teams working on the transplantation. The donor and the patient had to be located very close to each other during these operations, because there was no practical way of preserving the kidneys for any substantial period of time after they had been removed from the donor body and before they were transplanted into the patient's body. The procedure was always therefore an emergency procedure and was fraught with risks as well as difficulties. Similar problems and the same difficulties have applied to the transplantation of other organs, such as a heart or liver.

It has always been a goal in the preservation of human organs to make it possible to keep the organ alive for many hours and up to several days after harvesting the organ from the donor body. This would make it possible to use cadaver's kidneys, hearts, and livers and to have the harvesting operation and the transplant operation spaced apart by several days. The transplantation, therefore, could be an elective rather than an emergency procedure. Since additional time could be available, it would become possible to match the donor and recipient by tissue typing; unrelated donors who have proved compatible by tissue typing are generally as successful as donors who are related to the recipient. If additional time were available, and the organ could be preserved for a longer period of time, it would become possible for the recipient to wait at home until the correctly matched kidney or kidneys would become available. Furthermore, extra time would enable a single team of surgeons to do the harvesting operation and the transplanting operation. The surgery could be spaced apart by several days if necessary. Alternatively, the use of two teams could still be possible, but they would not need to be as close to each other at the time, for the organ to be transported substantial distances during the preservation time when the organ is being perfused outside of the body prior to transplanting.

Previously, organs have been transported from the donor to the recipient by the use of common ice coolers. The organ is placed into static cold storage and delivered by hand from one hospital to another. The use of common ice coolers was developed because of the convenience of finding packaged ice at locations remote from the hospital. Unfortunately, the transport of kidneys in static cold storage has resulted in problems. Typically, intercellular acidosis will occur. Intercellular acidosis is the build-up of acids and other toxins in the organ. Eventually, these toxins will damage or destroy the organ. Another problem is the inducement of hypothermia into the stored organ. Over a period of time, the cold static storage may cause the organ cells to begin swelling and cause eventual failure. Acute tubular necrosis, or post transplant early organ dysfunction, occurs much more frequently in patients where the kidney is placed in static cold storage, causing the patient to require post transplant dialysis. As such, over the years, it was determined that pulsatile pumping action is necessary to maintain organ viability so as to preserve the organ for a longer period of time.

U.S. Pat. Nos. 3,632,473 and 3,753,865 issued to Folkert O. Belzer et al. Dr. Belzer was an early pioneer in preservation technology for effectively storing human organs. These patents describe a system that incorporates the transfer of organs, such as kidneys, hearts, livers or other organs from the donor's body into a perfusion chamber where human plasma, kept in constant supply and preferably fortified with hormones and other substances, as pumped through the organ. In the perfusion chamber, the organ functions generally as it would in the body. For example, the kidneys in the perfusion chamber produce urine. The system maintained the organ at low temperatures so that the organ's activity is kept at a minimum. The plasma, which is circulated through the organ, is recirculated and oxygenated. The pH of the plasma is adjusted by a supply of carbon dioxide. Dr. Belzer's system utilized careful filtering so as to enable the plasma to be kept free from foreign matter.

In Belzer's system, the pumping of the plasma through the organ is done by pulsatile pump such that pulses similar to those produced by the human heart are employed to force the cold plasma through the organ. Pressure is controlled with the aid of a damper having an air spring. The operation of the apparatus thus resembles the operation in the human body, but differs in the fact that it is being conducted at a very low temperature and in a type of controlled environment. In Belzer's system, in the transport and storage of kidneys, for example, it was not necessary to free the recirculated plasma from the small amount of urine produced during storage, for the freeing of the kidney from the urine can take place later in the patient's body after transplant. Pressures maintained on the organ are substantially those encountered by the organ in the human body. The flow of plasma through the organ is controlled in accordance with the pressure desired. In particular, the Belzer system utilized an air trap and the monitoring of the gauge pressures within the air trap so as to provide an indication of fluid pressure.

Another system that has been used for the preservation of organs during transportation is identified as a "MOX-100 Renal Preservation System" and is sold by Waters Instruments, Inc. of Rochester, Minn. This system was designed to provide long term, unattended perfusion of one or two kidneys in the hospital or in the operating room. This device utilizes a disposable cassette for organ storage which is molded and placed within the system. The cassette provides membrane oxidation with a static membrane and gravity perfusate flow of up to 600 milliliters per minute. A complete circulatory system is provided including an arterial reservoir, a pump head, a heat exchanger, a bubble trap, a venous reservoir, a plasma flow meter, and a membrane oxygenating sack. The overall system connects the pulsatile pump chamber and gas and refrigeration sources to this cassette. The system includes visual and audio alarm systems which indicate pressure or temperature problems or input power failures.

In Belzer's system and in Water's system, the fluid pressure to the organ is delivered mechanically. Additionally, each system utilizes a bubble trap so as to remove bubbles and gases from the organ preservation fluid. As a result, fluid pressure is measured from the bubble trap which contains air as well as solution. As such, the pressure was not a true blood pressure, but rather a gauge pressure which is dampened by the air in the bubble trap. It has been a common problem that both the Belzer system and the Waters system would occasionally damage the organ by over perfusing, causing irreparable damage by the application of pressures that were too great. There are no monitoring devices or safety devices to prevent the application of improper fluid pressure. Also, neither the Belzer or Waters system provides true dicrotic pulsatile action to the organ. As a result, accurate simulation of the human heart action was not accomplished by either of these systems.

It is an object of the present invention to provide a human organ preservation apparatus that effectively preserves the life of the organ outside of the human body.

It is a further object of the present invention to provide an human organ preservation apparatus that has the ability to salvage organs from non-heart beating donors.

It is a further object of the present invention to provide a human organ preservation apparatus that effectively monitors diastolic and systolic pressures effecting the organ.

It is another object of the present invention to provide a human organ preservation apparatus that effectively simulates dicrotic heart pumping action.

It is another object of the present invention to provide a human organ preservation apparatus that maintains the organ in a cold environment.

It is a further object of the present invention to provide a human organ preservation apparatus that simplifies monitoring and control requirements.

It is still a further object of the present invention to provide a human organ preservation apparatus that provides a continuous and uninterrupted fluid flow from the pulsatile pump to the organ.

These and other objects and advantages of the present invention will become apparent from a reading of the attached specifications and appended claims.

SUMMARY OF THE INVENTION

The present invention is an organ preservation apparatus that comprises an organ-receiving chamber, a pulsatile pump in continuous uninterrupted liquid communication with the organ-receiving chamber, and a fluid delivery tube interconnected between the organ-receiving chamber and the pulsatile pump. The pulsatile pump passes an organ preservation fluid to the kidneys placed in the organ-receiving chamber in a pressure waveform that resembles the internal pressure waveform and secondary dicrotic pulse pattern present inside the body with a normal heart beat. The fluid delivery tube serves to pass the organ preservation fluid through a membrane pre-filter in the organ-receiving chamber to the heat exchanger and back to the pulsatile pump.

The organ-receiving chamber includes an outer box having an insulated interior area, an organ-receiving cassette removably contained within the insulated interior area, and a lid detachably fastened to the outer box over the organ-receiving cassette so as to maintain the organ-receiving cassette in a sealed environment. The outer box has a rigid exterior wall. The exterior wall has an inside surface having a flexible ceramic insulating coating. The insulated interior area is formed within the outer box and also has a ceramic insulating coating. The insulated interior area has an ice-receiving volume that generally surrounds the organ-receiving cassette. The organ-receiving cassette includes a main organ-receiving area having a filtered membrane extending across the bottom of the main organ-receiving area, and a funneled sump area that is fastened below the bottom of the main organ-receiving area so as to pass the organ preservation fluid to the fluid delivery tube. A heat exchange surface is formed exterior of the funneled sump area and extends downwardly below the main organ-receiving area. The fluid delivery tube extends around this heat exchange stand tube surface within the insulated interior area.

The pulsatile pump comprises a bladder pump, a motor, and a cam system. The cam system is in driving connection with the motor such that the cam system rotates in relation to the motor. The cam system is in contact with a surface of the bladder pump so as to compress the bladder pump creating a dicrotic pulse waveform pressure pattern. The cam system particularly comprises a cam that is interconnected to the motor at a point on the surface of the cam, a cam follower in contact with the outer edge of the cam, and an actuator that is interposed between the cam follower and the bladder pump. The cam has an outer edge of varying radius from the point of connection to the motor. The cam follower follows the cam in such a manner that the cam follower moves to create a dicrotic pulse waveform pressure pattern. The actuator serves to compress the bladder pump in relation to the movement of the cam follower.

The bladder pump includes a flexible bladder, a first one-way heart action valve positioned on one end of the flexible bladder, and a second one-way heart action valve positioned at the other end of the flexible bladder. The first one-way heart action valve allows the organ preservation fluid to pass from the flexible bladder toward the organ-receiving chamber. The second one-way heart action valve is interconnected to the fluid delivery tube such that the organ preservation fluid passes into the flexible bladder. The pulsatile pump system further includes an adjustable backstop that is in contact with the bladder pump. The adjustable backstop is movable so as to control the interior volume of the bladder pump. A closed circuit fluid passageway is connected to the bladder pump and extends in valved relationship to the organ-receiving chamber. This closed circuit fluid passageway forms a continuous uninterrupted liquid pathway, void of any air and without the use of a bubble trap. A flow through pressure transducer is connected to the fluid passageway for measuring the systolic, diastolic, and mean fluid pressure. This pressure transducer produces a non-damped pressure waveform signal indicative of such fluid pressures inside the body's circulatory system.

An automated sensored manifold is connected in valved relationship to the closed circuit fluid passageway. This automated sensored manifold has a first outlet and a second outlet for fluid delivery to the organ-receiving chamber. In actual use, one outlet is connected to one kidney and the other outlet is connected to another kidney within the organ-receiving chamber. The automated sensored manifold has a first valve external of the organ-receiving chamber for controlling the organ-preservation fluid flow from the closed circuit fluid passageway to the first outlet. The automated sensored manifold also has a second valve that is external to the organ-receiving chamber for controlling the organ-preservation fluid flow from the closed circuit fluid passageway to the second outlet. The automated sensored manifold includes a hydrophobic microporus membrane that is connected to the closed circuit fluid passageway. This hydrophobic microporus membrane serves to sieve gas from the closed circuit fluid passageway and to effectively remove bubbles from the organ preservation fluid while maintaining a constant fluid pressure. As a redundant safety device, an ultrasonic bubble detector transducer is positioned on the closed circuit fluid passageway between the hydrophobic microporus membrane and the organ-receiving chamber. This ultrasonic bubble detector transducer detects bubbles in the organ preservation fluid. The ultrasonic bubble dector transducer is interconnected to the motor controller such that the motor stops upon a detection of a bubble within the organ preservation fluid. A pressure relief valve is also provided on the automated sensored manifold so as to allow excess fluid pressure to exit the system. This eliminates to possibility of excessive perfusing and prevents damage to the kidney.

A visual display is connected to the pressure transducer so as to constantly display the systolic, diastolic, and mean fluid pressures effecting the preserved organ. The visual display is also connected to a temperature transducer in the organ-receiving chamber so as to provide a constant monitor of temperatures within the organ-receiving chamber. A strip chart recorder is interconnected to the pressure transducer so as to permanently record pressure information over time. A communications system and an alarm system is also provided so as to alert medical personnel, via onboard computer modem, of the need for attention to the organ being preserved.

DETAILED DESCRIPTION OF THE INVENTION

Figure 1:
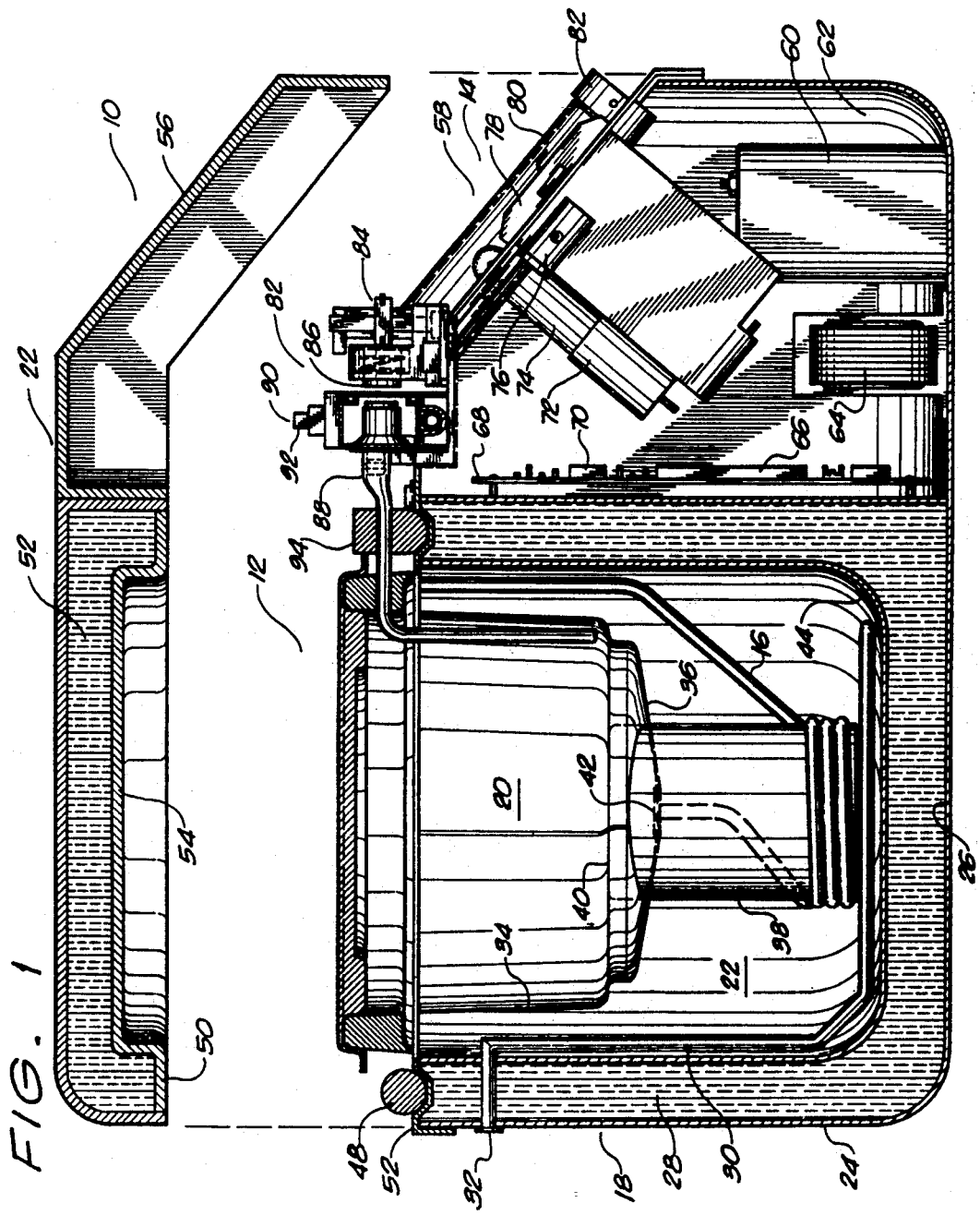
FIG. 1 is a cross-sectional view of the organ preservation apparatus in accordance with the preferred embodiment of the present invention showing, in exploded fashion, the lid as removed from the top of the box.

Referring to FIG. 1, there is shown at 10 the organ preservation apparatus in accordance with the preferred embodiment of the present invention. The organ preservation apparatus 10 comprises an organ-receiving chamber 12, a pulsatile pump 14, and a fluid delivery tube 16. As will be described hereinafter, the pulsatile pump 14 is in fluid communication with the organ-receiving chamber 12. The pulsatile pump 14 serves to pass an organ preservation fluid to the organ-receiving chamber 12 in a dicrotic pulse pattern. The fluid delivery tube 16 is interconnected between the organ-receiving chamber 12 and the pulsatile pump 14 so as to pass the organ preservation fluid from the organ-receiving chamber 12 to the pulsatile pump 14.

The organ-receiving chamber 12 includes an outer box 18, an organ-receiving cassette 20, and a lid 22. The outer box 18 includes an insulated interior area 22. In normal use, this insulated interior are 22 contains the organ-receiving cassette 20 along with a supply of ice. The organ-receiving cassette 20 is a disposable cassette that is removably contained within this insulated interior area. The organ-receiving cassette 20 is made of a molded plastic material. Typically, the organ-receiving cassette 20 is made of PETG plastic. The outer box 18 has a generally rigid exterior wall 24 that forms the exterior of the organ preservation apparatus 10. This rigid exterior wall 24 has a generally rectangular configuration. The exterior wall 24 can be made of a rigid molded plastic. The exterior wall 24 should be sufficiently rigid to withstand the forces imparted upon it during the transportation of the organ preservation apparatus 10. The rigid exterior wall generally surrounds the organ-receiving chamber 12, the pulsatile pump 14, and the fluid delivery tube 16.

Importantly, on the inside of the rigid exterior wall 24 is a flexible ceramic insulating coating 26. The ceramic insulating coating is applied, in a layer, to the inside of the exterior wall 24. This flexible ceramic insulating coating is a space age technology that was brought about by the development of the space shuttle. The flexible ceramic insulating coating is manufactured and sold by Insul-Coating Company of Houston, Tex. The flexible ceramic insulating coating, when applied to the inside of the exterior wall 24 effectively prevents heat intrusion from entering into the box 18. This flexible ceramic insulating coating is also applied to the exterior of the insulated interior area 22. The flexible ceramic insulating coating is applied to the insulated interior area so as to retain the cool temperatures caused by the filling of the insulated interior area 22 with ice. A foam insulation 28 may be interposed between the exterior wall 24 and the insulated interior area 22 so as to provide additional and further insulation. The foam insulation 28 can also provide shock absorption to the organ preservation apparatus. After experimentation, it was found that the arrangement of insulation described herein enabled the ice to maintain an effective cooling temperature for greater than ten hours without replacement. In the scheme of organ preservation, the ability to retain the cool temperatures of the ice for a longer period of time enables the organ to be preserved for a longer period of time. Additionally, the ability to avoid ice replacement within the insulated interior area 22 helps to avoid exposure of the organ to the external environment.

It can be seen that an external refrigeration connection 30 opens at 32 at the exterior wall 24 of the outer box 18. This external refrigeration connection 30 communicates with the insulated interior area 22. A suitable refrigeration unit can be connected to the external refrigeration connection so as to provide additional cooling capacity to the insulated interior area 22. This cooling capacity can be introduced without the need to open the organ preservation apparatus 10 and to expose the organ to the external environment.

It can be seen that the insulated interior area 22 includes an ice-receiving volume that generally surrounds the organ-receiving cassette 20. This is in contrast to prior art devices in which the organ-receiving cassette is maintained separate from (i.e., generally above) the ice-receiving volume. In prior art technology, the organ-receiving cassette was maintained at a different level than the ice. The cool temperatures were imparted to the organ-receiving cassette through heat exchange with the tubing running through ice or refrigeration to the organ-receiving cassette. The present invention is an improvement over these prior technologies by placing the organ-receiving cassette at a level in which the ice can generally surround the organ-receiving cassette. As such, even in the event of a failure of the refrigeration system, the organ will be maintained in cold static storage within the organ-receiving cassette.

The organ-receiving cassette 20 comprises a main organ-receiving area 34, a funneled sump area 36, and a heat exchange stand tube surface 38. The main organ-receiving area is a molded plastic area that has a suitable volume for receiving two (2) kidneys or other organs. The main organ-receiving area 34 is fitted within the insulated interior area 22. The main organ-receiving area includes a membrane 40 extending across the bottom of the main organ-receiving area. The membrane 40 acts as a pre-filter. It also provides the doctor with a surface to suture the kidney to. When it is necessary to transport the kidney within the organ-receiving cassette 20, it is generally necessary to fix the position of the kidney so that it does not move about. The felted fibrous membrane 40 provides such a surface to suture the kidney to, so that the kidney is stabilized during transit. This felted fibrous membrane 40 also serves to filter out dried blood cells or fat globules from the circulation system. A funneled sump area 36 is formed below the membrane 40. This funneled sump area 36 receives the drainage from the circulation system and from the kidney within the organ-receiving cassette 20. As organ preservation fluid passes from the kidney contained within the main organ-receiving area, the slanted walls of the sump area 36 delivers the fluid into the opening 42 of the fluid delivery tube 16. A heat exchange stand tube surface 38 is formed exterior of this funneled sump area 36 and extends downward into the insulated interior area 22. In normal usage, this heat exchange stand tube surface 38 will be surrounded with ice. By wrapping the fluid delivery tube 16 around the exterior of the heat exchange stand tube surface 38 (in the manner illustrated in FIG. 1), additional heat exchange effects occur between the ice within the insulated interior area 22 and the organ preservation fluid contained within the fluid delivery tube 16. The fluid delivery tube 16 is a flexible plastic tubing of suitable length for wrapping around the heat exchange stand tube surface 38. As shown in FIG. 1, the heat exchange stand tube surface 38 is of a cylindrical configuration, although this should not be construed as a limitation on the present invention. The end of the heat exchange stand tube surface 38 should be in close proximity to the bottom 44 of the insulated interior area 22.

In FIG. 1, it can be seen that the lid 22 of the organ preservation apparatus 10 is fitted across the top surface of the organ-receiving chamber 12. The lid 22 also has a rigid exterior surface 46 of a material similar to that of the rigid exterior wall 24 of the outer box 18. A suitable seal 48 is interposed between the bottom edge 50 of the lid 22 and the top edge 52 of the outer box 18. When the lid 22 is affixed in position, the seal 48 will preserve the cool temperatures within the interior of a organ-receiving chamber 12 and to prevent contamination from entering into the organ-receiving cassette 20. The lid 22 includes a suitable flexible ceramic insulating coating along the inner surfaces of the lid 22. This insulated surface corresponds to the area of the organ-receiving chamber 12. Suitable latches are provided so as to secure the lid 22 in position over the exterior of the organ-receiving chamber 12. When the lid 22 is secured over the organ-receiving chamber 12, the organ preservation apparatus 10 is in suitable condition for transportation. The organ preservation apparatus 10 thus becomes a sealed unit that can be carried and transported easily. The composition of material that is used to make the outer box 18 and the lid 22 is of a strong but lightweight material. Ultimately, the overall weight of the organ preservation apparatus 10 is much less than any prior art pulsatile preservation apparatus. The ceramic insulating coatings used so as to maintain the cool temperatures within the organ-receiving chamber 12 have been selected because the coatings are lightweight and provide significant insulating capacity. It can further be seen that a foam insulation 52 is contained within the area between the interior wall 54 and the exterior wall 46 of lid 22. Another portion 56 of lid 22 extends, in sealed fashion, over the control panel for the organ preservation apparatus 10 of the present invention.

FIG. 1 further shows the interior components of the control panel 58 of the present invention. To provide power to the system, a twelve-volt battery 60 is contained on the interior 62 of control panel area 58. A transformer 64 is also positioned within this interior area 62. The use of the battery 60 allows the organ preservation apparatus 10 to be transported from place to place without the need for external electrical power. However, a standard 115-volt electrical system has been incorporated within the apparatus of the present invention as a backup system if the battery 60 should become dead. When the apparatus 10 is placed in the hospital environment, or placed in proximity to an electrical outlet, then the electrical system can rely upon a standard 115-volt alternating current.

A computer monitoring system 66 is provided on circuit panel 68 within the interior area 62 of the control panel 58. The computer monitoring system, as will be described hereinafter, monitors the various conditions effecting any organ contained within the organ-receiving chamber 12. The computer monitoring system can monitor temperature, pressure, power requirements, fluid flow, and other items. The computer monitoring system 66 can transmit such information to a display located on the surface of the control panel 58. It can also transmit such information to a strip recorder so as to provide permanently recorded information concerning the conditions affecting the organ within the organ preservation chamber 12 over a period of time.

A motor controller 70 is also provided on the circuit panel 68. The motor controller 70 maintains the motor which operates the pulsatile pump (to be described hereinafter) at a constant sixty beats per minute. In order to maintain the viability of the organ contained within the organ-receiving chamber, it is important to provide a pulsatile pumping action of exactly sixty beats per minute. The use of the electronic motor controller 70 provides this constant sixty beats per minute regardless of resistance between the motor and the pump. In the preferred embodiment of the present invention, a 66 to 1 gear ratio is provided. The use of this motor controller adds power to the motor if the resistance starts to reduce the pumping action below sixty beats per minute. As such, the motor controller 70 maintains and assures a constant sixty beats per minute pumping rate, regardless of any reasonable resistance to such pumping action.

A micro-motor 72 is electrically connected to the motor controller 70. The micro-motor 72 is an aircraft standard motor of relatively small size but high power output. The high power output is necessary so as to maintain the sixty beats per minute pulsatile rate under all conditions of resistance. The micro-motor 72 is also designed so as to be operated in extremely cold temperatures. Prior art technologies incorporated standard electric motors that did not have the capacity to operate efficiently at temperatures below 4020 F. The aircraft style micro-motor 72 is particularly designed for operation at low temperatures or at various temperature extremes. The motor 72 is powered by the battery 60. A gear head 74 connects the motor 72 with the pulsatile pump 14. As described herein previously, the gear head 74 provides a 66 to 1 gear ratio between the motor 72 and the pulsatile pump. The gear head 74 also actuates the cam mechanism so as to provide the dicrotic pulse pattern for the pumping action.

A linear potentiometer is also provided in association with the control panel 14. A linear potentiometer 76 provides an electronic output of fluid flow through the pump. The linear potentiometer is spring loaded and connected to the backstop of the pump (to be described hereinafter). This linear potentiometer provides an output, to the computer monitoring system 66, of the amount of fluid displacement. Calculations are carried out within the processor of computer 66 to provide an output corresponding to the fluid flow through the pump. In contrast with the prior art, the electronic monitoring of fluid flow is carried out in a better non-intrusive manner than the mechanical methods of flow measurement in the prior art. The fluid flow measurement scheme of the present invention is not invasive of the fluid flow within the system. Rather, the flow measurement is carried out external of the fluid flow system.

FIG. 1 shows the backstop 78 that rests against the bladder pump 80. The backstop 78 is an adjustable mechanism that is used to regulate the volume of fluid within the bladder pump 80. This configuration is described in greater detail in connection with FIG. 3. A one-way heart action valve 82 is provided at one end of the bladder pump 80 so as to allow fluid to flow from the fluid delivery tube 16 into the bladder pump 80. The one-way heart action valve 82 prevents any fluid within the bladder pump 80 from passing from the bladder pump 80 back into the fluid delivery tube 16. The interaction of the motor 72, the gear head 74, the backstop 78, and the bladder pump 80 serves to send the organ preservation fluid toward any organ contained within the organ-receiving cassette 20. Importantly, the present invention incorporates the use of the automated sensored manifold 82 so as to control the closed circuit fluid flow to the organs within the organ-receiving cassette 20 and to cause any bubbles or gases to be removed from the closed circuit fluid flow.

The automated sensored manifold 82 includes an external flow control actuator 84 that has suitable mechanisms for actuation. It can be seen that the flow control actuator 84 has a plunger 86 that can be actuated so as to terminate fluid flow to one or both kidneys. When activated, the plunger 86 closes the fluid flow to the tube 88. When opened, fluid flows in a normal fashion through the tube 88. The plunger 86 is external to the organ preservation fluid pathway. In contrast to prior art systems, the present invention allows the opening and closing of fluid flow pathway to the organ from an area external to the organ-receiving cassette 20. In this manner, the attendant to the device never has to come into contact with the organ. Typical prior art techniques used clamps, and other mechanisms, to stop the fluid flow. The use of the external flow control actuator as part of the present invention eliminates the need to ever enter the receiving chamber 20 for the purpose of stopping the fluid flow to one or both kidneys. As will be described hereinafter, the automated sensored manifold 82 can divide the pulsatile fluid flow into two pathways. In normal organ preservation techniques, two kidneys are preserved simultaneously. Each of the fluid pathways would transmit organ preservation fluid to a separate kidney (or other organ).

An important feature of the present invention, that is not shown in prior art technology, is the use of the hydrophobic microporus membrane 90 in conjunction with the automated sensored manifold 82. The hydrophobic microporus membrane acts as a sieve for separating gas from liquid the aqueous fluid. The hydrophobic microporus membrane removes any gases from the aqueous fluid flow. It is important to organ preservation that gases not enter the organ or block the aqueous fluid flow. In prior art technology, bubble traps were used so as to trap the air in an area away from the fluid delivery tubes, yet within the fluid flow system. The use of the hydrophobic microporus membrane 90 eliminates the need for the bubble traps by automatically venting-/eliminating any air or other gases from the system and, at the same time, maintains a continuous pressurized uninterrupted aqueous liquid circulation circuit between the pump 80 and the organ within the organ-receiving cassette 20.

In the event that a bubble remains after the liquid passes through the hydrophobic microporus membrane 90, an ultrasonic air bubble transducer 94 is connected to the fluid flow 88. The ultrasonic bubble transducer 94 clamps onto the tubing but does not interrupt fluid flow. A circuit drives one transducer which projects ultrasonic energy across the tubing and its contents. A second transducer acts as a receiver, sensitive to the ultrasonic energy transmitted across the fluid path. When a bubble passes through the sensor, the path of acoustic energy is interrupted. From the received transducer signal, the circuit is capable of not only detecting the presence of bubbles in the fluid, but can also accurately differentiate bubble sizes and empty line conditions. Such an ultrasonic air bubble sensor is manufactured by Zevex, Inc. of Murray, Utah. In the event of a bubble passing through the fluid delivery tube 88, the ultrasonic bubble transducer 94 will transmit a signal to the motor controller 70 so as to shut down the pumping system. Since this occurs virtually instantaneously, the air bubble will not reach the organ. When the motor 72 is shut down, the system reverts to a cold static storage system. The configuration of the one-way heart action valves, the hydrophobic microporus membrane, the pressure relief vales, and the bubble transducer, effectively prevents the system from injuring or excessively perfusing the organ.

As an additional feature of the present invention, a pressure relief valve is provided on the automated sensored manifold 82. This pressure relief valve is of a standard configuration. When the pressures in the fluid delivery tube 88 reach a certain level, the pressure relief valve will open up so as to reduce the pressures affecting the organ. The pressure relief valve may release fluid in amounts sufficient to bring the fluid pressures to a reasonable range. The pressure relief valve acts as an additional safeguard to further prevent injury to the organ or excess pressures from over perfusing the organ. The pressure relief valve further assists in the self-priming of the system.

Figure 2:
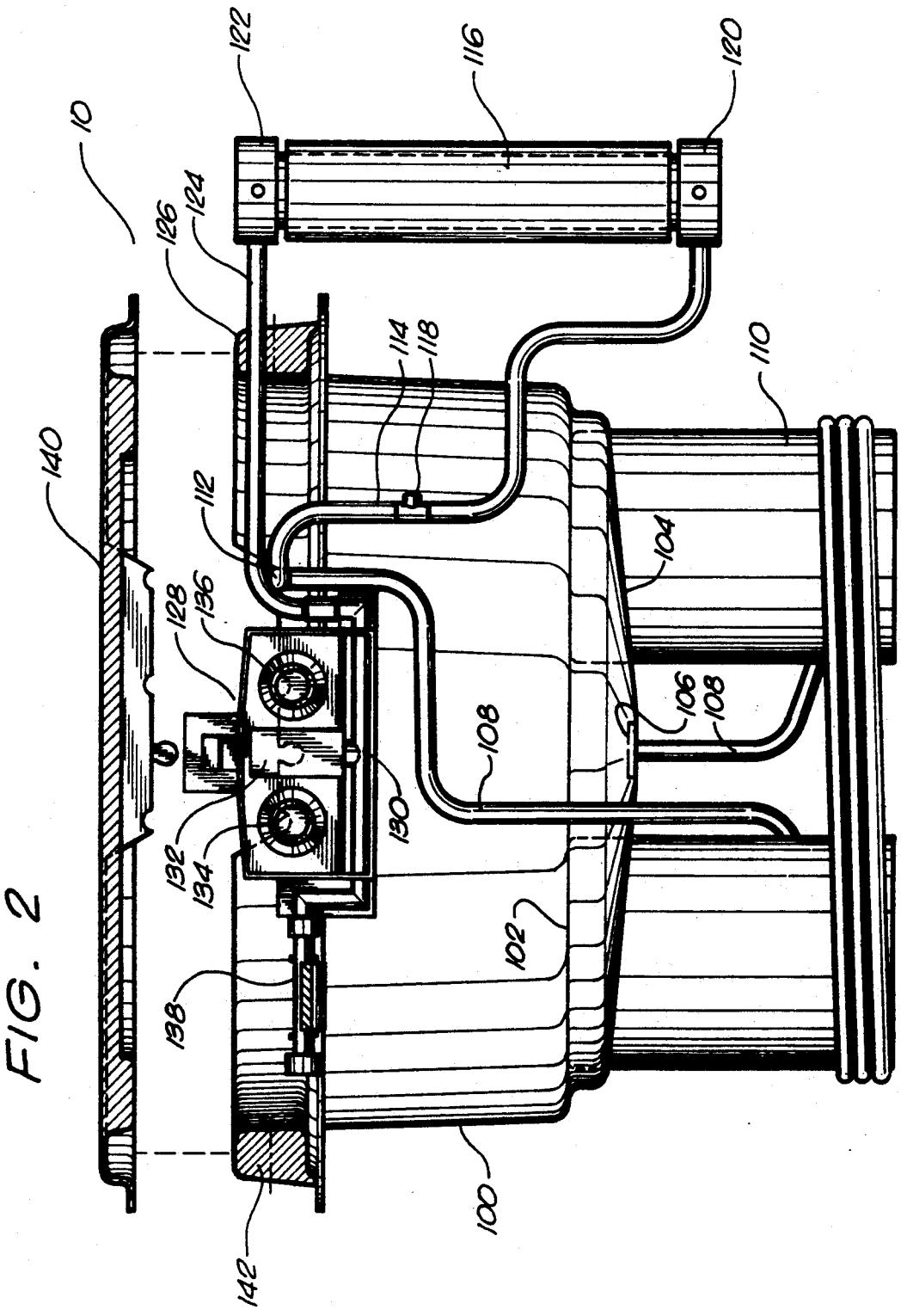
FIG. 2 is a view in side elevation showing the organ preservation cassette in accordance with the preferred embodiment of the present invention.

FIG. 2 shows the organ-receiving cassette and related items. In normal use, the items shown in FIG. 2, are the disposable items associated with the organ preservation apparatus 10. These disposable items are replaced after every kidney and other human organ transport. The replacement of these items is necessary so as to preserve the sterile conditions associated with organ transport and storage. Virtually all of the items shown in FIG. 2 are made of molded plastic materials. The organ-receiving cassette 100 is shown in its generally rectangular configuration having the felted membrane 102 at its bottom. It can be seen that the sump 104 directs fluid flow to the inlet 106 associated with the fluid delivery tube 108. Fluid delivery tube 108 extends around the heat exchange stand tube surface 110 of the organ-receiving cassette 100. By wrapping the fluid delivery tube 108 in the manner shown in FIG. 2, the fluid within the tube 108 is exposed for suitable heat exchange with any ice contained within the insulated interior of the outer box. After wrapping around the heat exchange stand tube surface 110, the fluid delivery tube 108 extends upward so as to connect at 112 to fluid delivery tube 114. The pumping action by the bladder pump 116 causes the organ preservation fluid within the fluid delivery tube 108 to pass in the pattern shown in FIG. 2. In the fluid delivery tube 114, a disposable lure thermistor temperature probe 118 is fitted. This temperature probe 118 is connected to the computer monitor 66 (shown in FIG. 1) so as to provide suitable temperature information as to the conditions of the organ preservation fluid within tube 114. If the temperature of the organ preservation fluid is too high, then a suitable signal is transmitted to the computer 66, and to the display panel, so as to warn the user to introduce additional ice into the insulated interior or to otherwise cool the interior of the system.

Any organ preservation fluid in tube 114 will pass into the bladder pump 116. Ultimately, the organ preservation fluid in the tube 114 will enter the one-wa heart action valve 120 at the bottom of bladder pump 116. The one-way valve 120 is a specially designed valve which allows the fluid to enter the bladder pump 116 while preventing the fluid from flowing downwardly from the bladder pump 116 into the tube 114. As can be seen, the bladder pump 116 includes an interior area that represents a pumping volume. By changing the amount of volume within the bladder pump 116, the amount of fluid that can be pumped by the system of the present invention can be correspondingly changed. Another one-way valve 122 is attached at the opposite end of the bladder pump 116. One-way valve 122 allows the organ preservation fluid to flow from the bladder pump 116 into the tube 124. The one-way valve 122 prevents any fluid from flowing from the tube 124 back into the bladder pump 116. The arrangement of the one-way valves 120 and 122 effectively resembles the valve action on human hearts. By using these one-way valves 120 and 122, a suitable unidirectional flow of organ preservation fluid is established.

Fluid delivery tube 124 extends from the pump 116 through the seal 126 between the display panel and the organ-receiving cassette 100. Tube 124 then passes toward the automated sensored manifold 128. It can be seen in FIG. 2 that tube 124 eventually passes to a branch connection 130 adjacent to the automated sensored manifold 128. One portion of the fluid within the tube 124 will pass into the central area of automated sensored manifold 128. The hydrophobic microporus membrane 132, at this location, separates any gases from the liquid flow. The organ preservation fluid will then be divided into two pathways. As can be seen, the automated sensored manifold 128 has a first outlet 134 and a second outlet 136. The fluid from the fluid delivery tube 124 will pass outwardly, toward the organ within the organ-receiving cassette 100 through these outlets 134 and 136. With the use of the valved action of the automated sensored manifold 128, the flow to the organs within the organ-receiving cassette 100 can be effectively controlled. Any gas will pass outwardly through the hydrophobic microporus membrane 132.

At the other end of the fluid delivery tube 124 is a disposable electronic pressure transducer 138. The organ preservation fluid will flow pass the branch 130 and into this pressure transducer 138. In contrast with prior art technologies, the use of the electronic pressure sensor 138 provides an effective measurement of diastolic and systolic fluid pressures. The prior art technologies always required the use of a bubble trap to remove any bubbles from the organ preservation fluid. However, whenever a bubble trap is used, an interrupted non-continuous liquid flow is created. As such, it is only possible to obtain a gauge pressure of the organ preservation fluid. The gauge pressure utilized in prior art technologies is quite different than the measurement of blood pressure. The measurement of blood pressure measures the systolic, diastolic, and mean pressures in the circulatory system. This more closely resembles the behavior of the blood within the human body. It was a common problem when measuring gauge pressure that the organ would eventually be damaged because of excessive perfusion, because the gauge pressure did not correspond accurately with the fluid pressures transmitted to the organ by pulsatile pumps. By using a closed uninterrupted fluid system, the present invention is able to measure a diastolic and systolic blood pressure while providing pulsatile pumping action. There is no air trap interruption of the closed circuit system of the present invention. The electronic flow-through pressure monitor 138 provides an electronic signal to the computer 66 of the present invention. This signal is then relayed, in the form of a visual display, of systolic and diastolic blood pressure, and can be continually monitored throughout the transport and storage of the organ within the system. Additionally, the pressure transducer 138 utilizes a lure lock fitting so that there is no need to prime the system prior to use. As such, the ability to use the electronic pressure transducer 138 within the system of the present invention is a significant improvement over prior art technologies of organ transportation and storage.

In FIG. 2, it can be seen that the organ-receiving cassette 100 has a clear see-through cover 140 that can be placed over the top of the cassette 100. This assures additional sealing of the system, prevents external contamination from occurring, and retains the organ preservation fluid within the cassette 100. The cover 140 can be fitted over seals 126 and 142 so as to provide a secure closed system.

Figure 3:
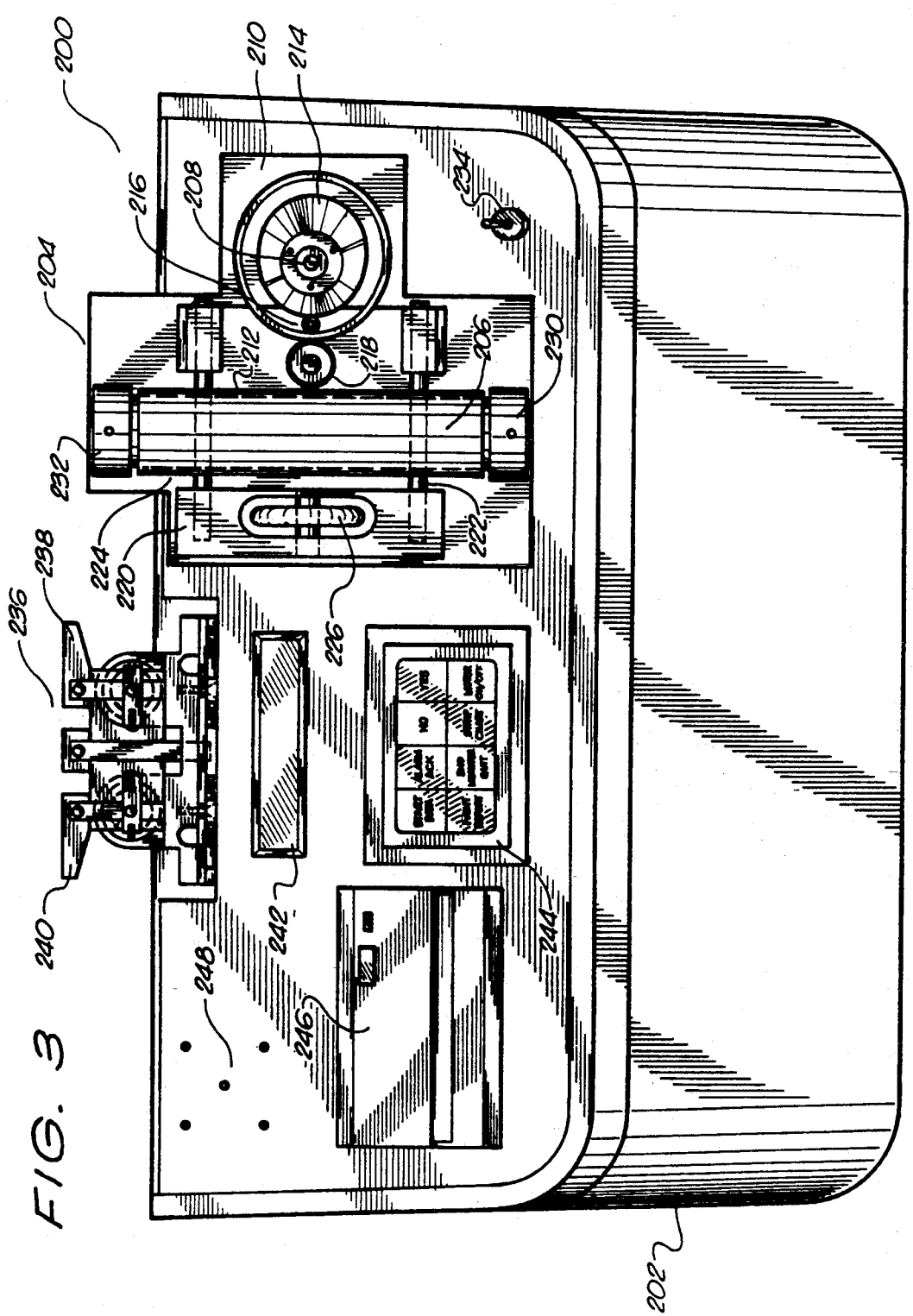
FIG. 3 is a frontal view in partial cross-section showing the organ preservation apparatus in accordance with the preferred embodiment of the present invention.

FIG. 3 shows the display panel 200 of the present invention. It can be seen that the display panel 200 is provided on the exterior surface of box 202 in a location opposite to the organ-receiving chamber. The display panel 200 is provided so as to provide humanly perceivable signals and controls as to the operation of the organ preservation system of the present invention. The battery, motors, computer, and controls are contained within the interior of box 202 rearward of the displays on the display panel 200.

In FIG. 3, an illustration is provided of the pulsatile pump system 204. It can be seen that the bladder pump 206 is detachably mounted on the display panel 200. A motor 208 is provided, rearward of the display panel 200, so as to drive a cam system 210. The cam system 210 is in such driving connection with the motor that the cam system 210 rotates in relation to the motor. The cam system 210 is in contact with a surface 212 of the bladder pump 206. The cam system 210 compresses the bladder pump 206 in a dicrotic pulse pattern.

The cam system 210 comprises a cam 214 which is interconnected to motor 208 at a central point. The cam 214 has an outer edge of varying radius from the point 208. It is important to the embodiment of the present invention that the shape of the cam 214 provides a dicrotic pulse pattern. The term "dicrotic pulse pattern" is the double spike effect of the heart. Prior art technologies provided pulsatile action that was not of the "double spike" effect. Prior art pulsatile pumping technologies relied on a single spike to resemble heart pumping action. After experimentation, it was found that the dicrotic pulse pattern more accurately resembled the actual pumping action of the heart.

A cam follower 216 is a bearing which is in rolling connection with the cam 214. The bearing 216 rolls and moves in a dicrotic pulse pattern by being in constant contact with the outer edge of the cam 214. An actuator 218 is interposed between the cam follower 216 and the bladder pump 206. Actuator 218 compresses the bladder pump 206 in relation to the movement of the cam follower 216. The rotation of the cam 214 at sixty revolutions per minute, and the movement of the actuator 218 in a dicrotic pulse pattern effectively creates a simulation of actual heart action. The compressing of the bladder pump 206 sends the fluid to the preserved organ in a manner closely resembling the actual pumping action of the heart.

It should be kept in mind that any kidneys that would be stored would be of various sizes. A small kidney will require less organ preservation fluid than would a large adult-sized kidney. Accordingly, it is important to be able to adjust the amount of organ preservation fluid that can be received by the bladder pump 216 and, hence, delivered to the organ. In keeping with this principle, an adjustable backstop 220 is provided. The adjustable backstop 220 can be moved along pathway 222 so as to be brought in contact with a surface 224 of bladder pump 206. A thumbwheel 226 can be provided so as to move the backstop 220 as desired. As the backstop compresses the surface 224 of bladder pump 206, the volume on the interior of bladder pump 206 is reduced accordingly. The linear potentiometer can provide the operator with a proper analysis as to the volume of fluid within the compressed bladder pump 206. A lock be is provided so as to prevent the backstop 220 from moving out of its position. As described herein previously, the bladder pump 206 has a first one-way heart action valve 230 at its bottom end and a second one-way heart action valve 232 at its top end. Fluid passes through these one-way heart action valves in a manner further resembling the actual pumping action of the heart.

A toggle switch 234 is provided as a safety switch. This is a locking toggle switch that prevents the organ preservation apparatus of the present invention from being inadvertently switched on or off.

The automated sensored manifold system 236 is shown as having the actuator levers 238 and 240 as extending outside of the organ-receiving chamber. These automated sensored manifold levers are located outside of the storage system so as to keep the attendant from touching anything within the organ-receiving cassette. The actuators allow the flow to each of the organs to be adjusted as needed. In addition, the use of the actuator levers 238 and 240 assists in the installation of the kidney. It is always necessary to install one kidney at a time within the organ-receiving cassette. By closing the actuator lever for each kidney, during installation of the kidneys, the correct pressures can be properly adjusted for each of the kidneys.

A liquid crystal display 242 is placed on the center of the display panel 220. The liquid crystal display 242 provides the operator of the organ preservation apparatus a constant input of information concerning the conditions affecting the stored organ. The liquid crystal display 242 is connected to the computer in such manner that any signal generated by the computer is displayed on the display 242. The display 242 will present constant information concerning diastolic and systolic fluid pressures, temperature within the organ-receiving chamber, fluid flow, and other information. The constant feedback of information is an important feature of the present invention. For example, during the initial installation of the organ, the blood pressure should be kept at a desired level. However, after the fluid begins flowing through the organ, the organ will open up and the blood pressure will decrease somewhat. In order to maintain the blood pressure at a constant level, it is necessary to adjust the backstop 220 by rotating the thumbwheel 226. The visual display 242 will then provide the operator with the necessary information so as to allow the proper adjustments to be made so as to control the correct fluid flow and pressure acting on the organ. Also, if the temperature within the chamber begins to warm, the display 242 will provide an indication to the operator that additional ice or refrigeration must be provided to the storage chamber.

A touchpad membrane switch control system 244 is provided for the onboard computer 66. This touch control system provides interactive information with the computer so that the operator can properly control the operation of the organ preservation apparatus. The display 242 can be an interactive display in which the operator may need to key in information such as "yes" or "no". The use of this touchpad display 244 greatly simplifies the operation and use of the organ preservation apparatus. A strip chart recorder 246 is also provided on the display panel 200. The strip chart recorder can record information, such as that shown on display 242, over a period of time. This strip chart recorder 246 can be used to keep a constant and permanent record of conditions during organ transport. If a failure occurs during the transport of an organ, then the strip chart can be referenced so as to determine the nature of the failure. The strip chart can be maintained in the records for any future references that may be necessary and for further diagnostics on the kidney or other human organs or organ transport system.

Various power indicator lights 248 are provided so as to indicate the operation of the system. The display panel 200 can also be modified in various ways. For example, a suitable audio or visual alarm system can be incorporated into the design of a panel so as to provide immediate information as to emergency conditions. Additionally, a communications package can be integrated with the computer and will incorporate a number of telephone numbers that the system could call in the event of an emergency. If the parameters of operation get outside of a given range, then an alarm goes off. If the system does not return to its proper operating parameters, the communications package could begin dialing the telephone numbers so as to notify the doctors or medical technicians. The doctors or medical technicians could call the machine back to get the detailed information as to what was happening with the stored organ.

It is an important feature of the present invention that the organ preservation apparatus provides a fail/safe technique for preserving the organ. As stated previously, pressure relief valves, bubble detector sensors, and hydrophobic microporus membranes are utilized so as to prevent the organ from being damaged. Also, backup systems are incorporated in case of a failure of one or more components of the system. Very importantly, however, if the entire system fails, then the organ is not permanently damaged. Throughout the operation of the system, if failure occurs, then the system simply reverts to standard cold static storage. In the worse case possibility, the organ remains available for transport in standard fashion.

Figure 4:
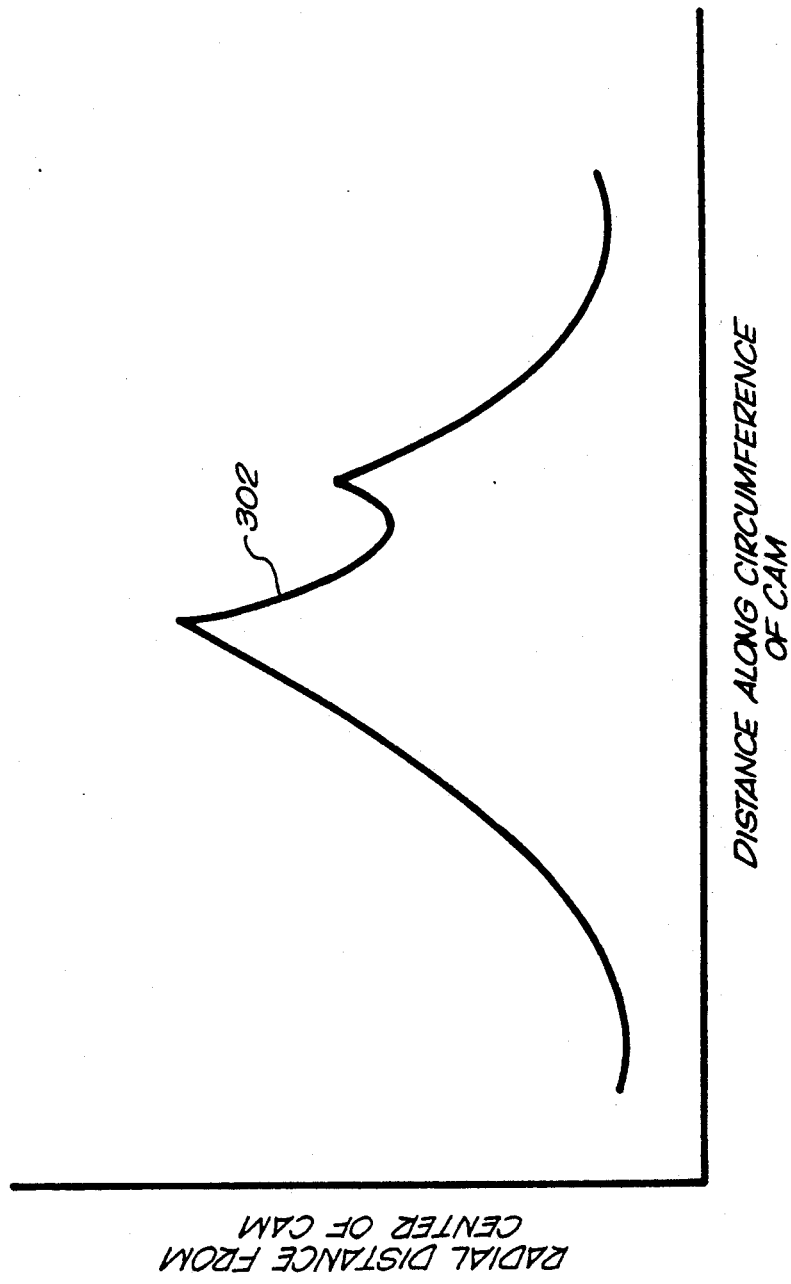
FIG. 4 is a graph illustrating the dicrotic pulse pattern of the pulsatile pump of the present invention.

FIG. 4 illustrates the shape of the cam 214. In FIG. 4, the radial distance from the center of the cam changes throughout the circumference of the cam. It can be seen that the graph of FIG. 4 illustrates a dicrotic pulse waveform. Area 302 is called the "dicrotic notch". All human heartbeats create this dicrotic notch pressure waveform within the circulatory system. In order to create a system that more accurately reflects the actual pumping operation of the heart and the pumping action in the human body, it is very important to duplicate the dicrotic notch waveform within the closed circuit pumping system. By shaping the cam in the manner illustrated in FIG. 3 and shown in FIG. 4, the ability to compress the bladder pump 206 in the manner of the dicrotic pulse is accomplished.

The present invention can incorporate many types of organ preservation solutions. However, the preferred organ preservation solution is of a type described and developed by Folkert O. Belzer which utilized a kidney perfusate that contained Sodium Gluconate—100 mM/liter, includes hydroxyethyl starch and other additives (adenosine, glutathione, potassium phosphate, magnesium sulphate). Initial studies of this preservation solution indicated that it had a favorable metabolic effect on the kidney. This solution is pH stable. However, various other preservation solutions could be utilized within the system of the present invention.

The present invention is an organ preservation apparatus that effectively duplicates the pumping operation of the heart during the storage of organs. Although the present invention has been described in conjunction with the storage and transportation of kidneys, it is adaptable to a wide variety of other organs such as hearts, pancreases, livers, and other human organs.

In contrast with prior art technologies, the present invention is a significant improvement. First, the present invention perfuses the organ with a pulsatile dicrotic pulse patterns for preserving the organ. The present invention maintains the organ in a cold sealed environment. The present invention provides constant monitoring of the organ and constant input to the operator of the system. Importantly, accurate diastolic and systolic fluid pressures are measured. The present invention has overcome the problems of prior art systems by accurately measuring diastolic and systolic pressures, instead of gauge pressures from a system containing a compressed gas which damps the pressure reading. Prior art systems relied on gauge pressure since bubble traps and interrupted fluid delivery pathways were used. The use of the one-way heart action valves, the adjustment mechanisms, the air bubble removal and monitoring of the present invention make it virtually impossible to damage the organ during operation of the organ preservation system. The organ preservation apparatus, and the associated equipment, is relatively lightweight and transportable. Each of the items of the organ preservation system are self-contained and transportable. Therefore, the present invention offers significant improvements over any prior art organ storage, preservation, and transport systems available.

The foregoing disclosure and description of the invention is illustrative and explanatory thereof. Various changes in the details of the illustrated apparatus may be made within the scope of the appended claims without departing from the true spirit of the invention. The present invention should only be limited by the following claims and their legal equivalents.

I claim:

1. An organ preservation apparatus comprising:
   an organ-receiving chamber;
   a pulsatile pump means in fluid communication with said organ-receiving chamber, said pulsatile pump means for passing an organ preservation fluid to said organ-receiving chamber in a dichrotic pulse pattern, said pulsatile pump means comprising:
   a bladder pump;
   a motor;
   cam means in driving connection with said motor such that said cam means rotates in relation to said motor, said cam means in contact with a surface of said bladder pump, said cam means for compressing said bladder pump in a dichrotic pulse pattern; and
   a fluid passageway connected to said bladder pump and extending in valved relation into said organ-receiving chamber, said fluid passageway forming a continuous uninterrupted liquid pathway;
   a pressure transducer conducted to said fluid passageway, said pressure transducer for measuring a diastolic fluid pressure and a systolic fluid pressure in said fluid passageway, said pressure transducer for producing a signal indicative of said diastolic and systolic fluid pressures; and
   fluid delivery means interconnected between said organ-receiving chamber and said pulsatile pump means for passing the organ preservation fluid from said organ-receiving chamber to said pulsatile pump means.

2. The organ preservation apparatus of claim 1, said organ-receiving chamber comprising:
   an outer box having an insulated interior area;
   an organ-receiving cassette removably contained within said insulated interior area; and
   a lid detachably fastened to said outer box over said organ-receiving cassette so as to maintain said organ-receiving cassette in a sealed environment.

3. The organ preservation apparatus of claim 2, said outer box having a rigid exterior wall, said exterior wall having an inside surface having a ceramic insulating coating, said insulated interior area formed within said outer box, said insulated interior area having a ceramic insulating coating.

4. The organ preservation apparatus of claim 2, said insulated interior area having an ice-receiving volume generally surrounding said organ-receiving cassette.

5. The organ preservation apparatus of claim 2, said organ-receiving cassette comprising:
   a main organ-receiving area having a membrane extending across a bottom of said main organ-receiving area; and
   a funneled sump area formed below the bottom of said main organ-receiving area, said funneled sump area for passing said organ preservation fluid to said fluid delivery means.

6. The organ preservation apparatus of claim 5, further comprising:
   a heat exchange surface formed exterior of said funneled sump area and extending downwardly below said main organ-receiving area, said fluid delivery means extending around said heat exchange surface in said insulated interior area.

7. The organ preservation apparatus of claim 1, said cam means comprising:
   a cam connected to said motor at a point on a surface of said cam, said cam having an outer edge of varying radius from said point;
   a cam follower in contact with said outer edge of said cam such that said cam follower moves in a dichrotic pulse pattern; and
   an actuator interposed between said cam follower and said bladder pump, said actuator for compressing said bladder pump in relation to the movement of said cam follower.

8. The organ preservation apparatus of claim 1, said bladder pump comprising:
   a flexible bladder;
   a first one-way valve positioned at one end of said flexible bladder, said first one-way valve for allowing said organ preservation fluid to pass from said flexible bladder to said organ-receiving chamber; and
   a second one-way valve positioned at another end of said flexible bladder, said second one-way valve interconnected to said fluid delivery mean such that the organ preservation fluid passes into said flexible bladder.

9. The organ preservation apparatus of claim 1, further comprising:
   an adjustable backstop means in contact with said bladder pump, said adjustable backstop means movable so as to control the interior volume of said bladder pump.

10. An organ preservation apparatus comprising:
    a bladder pump;
    a motor;
    cam means in driving connection with said motor such that said cam means rotates in relation to said motor, said cam means in contact with a surface of said bladder pump, said cam means for compressing said bladder pump in a dichrotic pulse pattern; and
    a fluid passageway connected to said bladder pump and extending in valved relation into said organ-receiving chamber, said fluid passageway forming a continuous uninterrupted liquid pathway;
    a manifold connected in valved relationship to said fluid passageway, said manifold having a first outlet and a second outlet for fluid delivery to said organ-receiving chamber, said manifold having a first valve external of said organ-receiving chamber for controlling organ preservation fluid flow from said fluid passageway to said first outlet, said manifold having a second valve external of said organ-receiving chamber for controlling organ preservation fluid flow from said fluid passageway to said second outlet; and
    fluid delivery means interconnected between said organ-receiving chamber and said pulsatile pump means for passing said organ preservation fluid from said organ-receiving chamber to said pulsatile pump means.

11. The organ preservation apparatus of claim 10, said manifold having a hydrophobic membrane connected to said fluid passageway, said hydrophobic membrane for sieving gas from said fluid passageway.

12. The organ preservation apparatus of claim 11, further comprising
    an ultrasonic bubble transducer positioned on said fluid passageway between hydrophobic membrane and said organ-receiving chamber, said ultrasonic bubble transducer for detecting a bubble in said organ preservation fluid in said fluid passageway.

13. The organ preservation apparatus of claim 12, said ultrasonic bubble transducer interconnected to said motor such that said motor stops upon the detection of a bubble in said fluid passageway.

14. The organ preservation apparatus of claim 1, further comprising:
    a visual display connected to said pressure transducer so as to show the diastolic and systolic fluid pressures, said visual display interconnected to a temperature transducer in said organ-receiving chamber so as to show a temperature in said organ-receiving chamber.

15. The organ preservation apparatus of claim 14, further comprising:
    a strip chart recorder interconnected to said pressure transducer and to said temperature transducer so as to permanently record pressure and temperature information over time.

16. An organ preservation apparatus comprising:
    an organ-receiving chamber;
    a pulsatile pump means in continuous uninterrupted liquid communication with said organ-receiving chamber, said pulsatile pump means for passing an organ preservation fluid in a pulsed pattern to said organ-receiving chamber, said pulsatile pump means comprising a fluid passageway extending in valved relationship to said organ-receiving chamber, said fluid passageway forming a continuous uninterrupted liquid pathway;

a manifold connected in valved relationship to said fluid passageway, said manifold having a first outlet and a second outlet for fluid delivery to said organ-receiving chamber, said manifold having a first valve external of said organ-receiving chamber for controlling organ preservation fluid flow from said fluid passageway to said first outlet, said manifold having a second valve external of said organ-receiving chamber for controlling organ preservation fluid flow from said fluid passageway to said second outlet, said manifold having a hydrophobic membrane connected to said fluid passageway, said hydrophobic membrane for sieving gas from said fluid passageway; and a fluid delivery means interconnected between said organ-receiving chamber and said pulsatile pump means, said fluid delivery means for passing said organ preservation fluid from said organ-receiving chamber to said pulsatile pump means.

17. The organ preservation apparatus of claim 16, further comprising:
a pressure transducer connected to said fluid passageway, said pressure transducer for measuring a diastolic fluid pressure and a systolic fluid pressure in said fluid passageway, said pressure transducer for producing a signal indicative of said fluid pressures.

18. The organ preservation apparatus of claim 16, further comprising:
an ultrasonic bubble transducer positioned on said fluid passageway between said hydrophobic membrane and said organ-receiving chamber, said ultrasonic bubble transducer for detecting a bubble in said fluid passageway.

19. An organ preservation apparatus comprising:
an organ-receiving chamber;
a pulsatile pump means in continuous uninterrupted liquid communication with said organ-receiving chamber, said pulsatile pump means for passing an organ preservation fluid in a pulsed pattern to said organ-receiving chamber, said pulsatile pump means comprising a fluid passageway extending in valved relationship to said organ-receiving chamber, said fluid passageway forming a continuous uninterrupted liquid pathway;
a pressure transducer connected to said fluid passageway, said pressure transducer for measuring a diastolic fluid pressure and a systolic fluid pressure in said fluid passageway, said pressure transducer for producing a signal indicative of said diastolic and systolic fluid pressures;
fluid delivery means interconnected between said organ-receiving chamber and said pulsatile pump means for passing said organ preservation fluid from said organ-receiving chamber to said pulsatile pump means; and
a visual display connected to said pressure transducer so as to show the diastolic and systolic fluid pressures, said visual display interconnected to a temperature transducer in said organ-receiving chamber so as to show a temperature in said organ-receiving chamber.

20. The organ preservation apparatus of claim 16, said pulsatile pump means comprising:
a bladder pump;
a motor; and
cam means in driving connection with said motor such that said cam means rotates in relation to said motor, said cam means in contact with a surface of said bladder pump, said cam means for compressing said bladder pump in a dichrotic pulse pattern.

21. The organ preservation apparatus of claim 20, said cam means comprising:
a cam connected to said motor at a point on a surface of said cam, said cam having an outer edge of varying radius from said point;
a cam follower in contact with said outer surface of said cam such that said cam follower moves in a dichrotic pulse pattern; and
an actuator interposed between said cam follower and said bladder pump, said actuator for compressing the bladder pump in relation to the movement of said cam follower.

22. An organ preservation apparatus comprising:
an outer box having an insulated interior area, said outer box having a rigid exterior wall, said exterior wall having an inside surface having a ceramic insulating coating, said insulated interior area formed within said outer box, said insulated interior area having a ceramic insulating coating;
an organ-receiving cassette removably contained within said insulated interior area;
a lid detachably fastened to said outer box over said organ-receiving cassette so as to maintain said organ-receiving cassette in a sealed environment;
a pulsatile pump means in fluid communication with said organ-receiving cassette, said pulsatile pump means for passing an organ preservation fluid in a pulsed pattern; and
fluid delivery means interconnected between said organ-receiving cassette and said pulsatile pump means for passing the organ preservation fluid from said organ-receiving cassette to said pulsatile pump means.

23. The organ preservation apparatus of claim 22, said insulated interior area having an ice-receiving volume generally surrounding the exterior of said organ-receiving cassette.

24. The organ preservation apparatus of claim 22, said organ-receiving cassette comprising:
a main organ-receiving area having a membrane extending across a bottom surface of said main organ-receiving area; and
a funneled sump area formed below the bottom of said main organ-receiving area, said funneled sump area for passing said organ preservation fluid to said fluid delivery means.

25. The organ preservation apparatus of claim 24, further comprising:
a heat exchange surface formed exterior of said funneled sump area and extending downwardly below said main organ-receiving area, said fluid delivery means extending around said heat exchange surface within said insulated interior area.

26. The organ preservation apparatus of claim 22, further comprising:
an external refrigeration connection opening at said exterior wall of said outer box, said external refrigeration connection in fluid communication with said insulated interior area.

* * * * *